(12) United States Patent
Hendriks et al.

(10) Patent No.: US 10,179,418 B2
(45) Date of Patent: Jan. 15, 2019

(54) SHAVING DEVICE FOR SKIN HAIRS (71) Applicant: KONINKLIJKE PHILIPS N.V., Eindhoven (NL)

(72) Inventors: Cornelis Petrus Hendriks, Eindhoven (NL); Werner Daniel Petrus Kauwenberg, Eindhoven (NL); Roland Alexander Van De Molengraaf, Eindhoven (NL); Denny Mathew, Eindhoven (NL); Sander Theodoor Pastoor, Eindhoven (NL); Rufus Eugen Deodatus Driessen, Eindhoven (NL); Paul Philip Thursfield, Eindhoven (NL); Mark Thomas Johnson, Eindhoven (NL); Frederick Maria Boekhorst, Eindhoven (NL); Willem Auke Westerhof, Eindhoven (NL); Daan Anton Van Den Ende, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 108 days.

(21) Appl. No.: 15/514,544

(22) PCT Filed: Sep. 22, 2015

(86) PCT No.: PCT/EP2015/071627
§ 371 (c)(1),
(2) Date: Mar. 27, 2017

(87) PCT Pub. No.: WO2016/046142
PCT Pub. Date: Mar. 31, 2016

(65) Prior Publication Data
US 2017/0291319 A1 Oct. 12, 2017

(30) Foreign Application Priority Data

Sep. 26, 2014 (EP) .................................... 14186632

(51) Int. Cl.
*B26B 19/38* (2006.01)
*A61B 18/20* (2006.01)
(Continued)

(52) U.S. Cl.
CPC .......... *B26B 19/388* (2013.01); *A61B 18/203* (2013.01); *B26B 19/143* (2013.01);
(Continued)

(58) Field of Classification Search
CPC . B26B 19/388; B26B 19/143; B26B 21/4056; B26B 21/222; B26B 21/4018; A61B 18/203
See application file for complete search history.

(56) References Cited

U.S. PATENT DOCUMENTS 5,182,857 A * 2/1993 Simon .................. A61B 18/203
132/118
5,706,582 A 1/1998 Hosokawa
(Continued)

FOREIGN PATENT DOCUMENTS

EP 0906814 A1 4/1999
EP 2116341 A1 11/2009
(Continued)

*Primary Examiner* — Hwei C Payer (57) ABSTRACT

The invention relates to a shaving device for skin hairs. The device comprises a skin-contacting surface structure (14, 15), a cutter (6) for cutting hairs in a hair-cutting area (16), a shape-changing smart material (7), and a controller for controlling activation of the shape-changing smart material during use of the shaving device. The shape-changing smart material is configured, arranged and effective to adapt the relative position and/or relative orientation between at least part of the skin-contacting surface structure (14) and at least part of the hair-cutting area (16).

15 Claims, 8 Drawing Sheets

(51) Int. Cl.
  *B26B 21/22* (2006.01)
  *B26B 21/44* (2006.01)
  *B26B 19/14* (2006.01)
  *B26B 21/40* (2006.01)

(52) U.S. Cl.
  CPC ........ *B26B 21/222* (2013.01); *B26B 21/4018* (2013.01); *B26B 21/4056* (2013.01); *B26B 21/443* (2013.01)

(56) References Cited

U.S. PATENT DOCUMENTS

| | | | |
|---|---|---|---|
| 6,009,623 A | 1/2000 | Orloff | |
| 6,173,498 B1 * | 1/2001 | Warrick | B26B 21/227 30/50 |
| 8,348,472 B2 | 1/2013 | Ackermann | |
| 9,364,961 B2 * | 6/2016 | Lelieveld | B26B 21/227 |
| 2006/0218804 A1 | 10/2006 | Noble | |
| 2007/0151108 A1 * | 7/2007 | Westerhof | B26B 21/4018 30/50 |
| 2008/0098603 A1 | 5/2008 | Noble | |
| 2016/0107323 A1 * | 4/2016 | Krans | B26B 19/388 30/123 |
| 2016/0242848 A1 * | 8/2016 | Moeskops | A61B 18/203 |
| 2017/0156796 A1 * | 6/2017 | Moeskops | A61B 18/203 |
| 2017/0196640 A1 * | 7/2017 | Moeskops | A61B 18/203 |
| 2017/0291319 A1 * | 10/2017 | Hendriks | B26B 19/143 |
| 2017/0325566 A1 * | 11/2017 | Franklin | A45D 26/0061 |

FOREIGN PATENT DOCUMENTS

| | | |
|---|---|---|
| GB | 1384422 A | 2/1975 |
| JP | 59200683 A | 11/1984 |
| JP | 2000167270 A | 6/2000 |
| JP | 2003181165 A | 7/2003 |
| WO | 9626046 A1 | 8/1996 |
| WO | 102009010603 A1 | 5/2010 |
| WO | 2011001395 A1 | 1/2011 |
| WO | 2013093772 A1 | 6/2013 |
| WO | 2013140309 A1 | 9/2013 |
| WO | 2014139968 A1 | 9/2014 |

* cited by examiner

SHAVING DEVICE FOR SKIN HAIRS

This application is the U.S. National Phase application under 35 U.S.C. § 371 of International Application No. PCT/EP2015/071627, filed on Sep. 22, 2015, which claims the benefit of International Application No. 14186632.7 filed on Sep. 26, 2014. These applications are hereby incorporated by reference herein.

FIELD OF THE INVENTION

The invention relates to a shaving device for skin hairs, which shaving device comprises:
- a skin-contacting structure comprising a skin-contacting surface structure for contacting a portion of skin during shaving of said skin by the shaving device; and
- a cutter for cutting hairs of said skin portion being contacted by said skin-contacting surface structure, said cutting taking place in a hair-cutting area defined by the shaving device.

The invention applies to shaving devices in which the cutter may or may not be driven to move for performing its cutting movements. In the case of shaving devices with cutters being drivable to move, these movements may be of various nature, such as reciprocating translative movement, (reciprocating and/or continuous) rotative movement, or a combination of reciprocating translative movement and (reciprocating and/or continuous) rotative movement. Furthermore, according to the invention, the cutter may be substantially exposed, or covered by external (cutting) members having hair openings therethrough, which external members may be rigid members or flexible members (such as foils). Other cutter types, such as for example laser beam cutters, are possible as well according to the invention.

As mentioned hereinabove, the shaving device defines a hair-cutting area, in which area the hair-cutting by the cutter actually takes place.

Thus, it will be readily appreciated that for a shaving device in which a cutter is driven to move for performing its cutting movements (as mentioned above), the said hair-cutting area is thus defined as the full working area reached by the actual hair-cutting parts (usually cutting edges) of the cutter during their driven (cyclic) movements. For example, a well-known type of shaving device, popularly termed "rotary shaver", has one (usually more than one) annularly shaped hair-cutting area defined by the rotative movement trajectories of cutting edges of an internal cutting member along a rigid external cutting member having openings therethrough. And, e.g., another well-known type of shaving device, popularly termed "reciprocating shaver", usually has a (curved) rectangularly shaped hair-cutting area defined by the reciprocating movement trajectories of cutting edges of an internal cutting member along an external foil having openings therethrough.

And it will be also readily appreciated that for a shaving device in which a cutter is not driven to move for performing its cutting movements (as mentioned above), the said hair-cutting area is thus defined by the instantaneous position, within the device, of the actual hair-cutting parts (usually cutting edges) of the cutter. For example, a well-known type of shaving device, popularly termed "razor blade system", which is used for wet shaving and which requires the user to move the razor blade(s) along his or her skin, has at least one linearly shaped hair-cutting area defined by the instantaneous position(s), within the device, of the cutting edge(s) of the razor blade(s).

And, furthermore, it will be readily appreciated how the said hair-cutting area is defined for other cutter types. For example, for a laser beam cutter, the hair-cutting area corresponds to the area where the laser beam of the laser beam cutter is focused, since that is the area in which the hair-cutting actually takes place.

BACKGROUND OF THE INVENTION

A major challenge in using such a shaving device is to obtain high "closeness" in shaving (i.e. to cut the hairs as close as possible relative to the skin), while avoiding skin irritation as much as possible. Increasing the closeness requires bringing the hair-cutting area closer to the skin, and this increases the likelihood that the cutter will damage the skin. Therefore, high closeness and low skin irritation are contradictory requirements. Improving the "closeness/irritation balance" requires special skills and additional shaving time from users. Some of the reasons are, e.g., that a user has to reckon with different properties of different parts of the treated skin (e.g. cheek, neck, etc.), as well as with the responsive location-dependent and time-dependent varying deformation behaviour of the treated skin during the treatment. Note that also, e.g., dynamic user handling forces during the treatment play a role. In addition, it is noted that these, and many other differences, vary from person to person, not only because different persons have different skin types and skin properties, but also because different persons have different device handling behaviour.

WO2013/140309A1 mentions the abovementioned closeness/irritation balance (see e.g. page 1 of WO2013/140309A1). In view of said balance, WO2013/140309A1 proposes to incorporate a force-generating member in a skin-engaging portion of a shaver to selectively adjust, during use of the shaver, the attracting force exerted on the skin of a user, thereby selectively influencing the degree of skin doming during use of the shaver (see e.g. page 2 of WO2013/140309A1).

SUMMARY OF THE INVENTION

It is an object of the invention to provide at least an alternative solution which makes it easier for users of a shaving device to obtain a close-to-the-skin shaving result with little or no skin irritation, in other words to obtain a favourable closeness/irritation balance.

Hence, the invention provides a shaving device for skin hairs, comprising:
- a skin-contacting structure comprising a skin-contacting surface structure for contacting a portion of skin during shaving of said skin by the shaving device;
- a cutter for cutting hairs of said skin portion being contacted by said skin-contacting surface structure, said cutting taking place in a hair-cutting area defined by the shaving device;
- a shape-changing smart material of a class of materials that can reversibly change their shape and/or dimensions in a controlled way as a result of an externally applied electric stimulus and/or as a result of an externally applied thermal stimulus and/or as a result of an externally applied magnetic stimulus and/or as a result of an externally applied chemical stimulus and/or as a result of an externally applied optical stimulus; and
- a controller for controlling activation of the shape-changing smart material during use of the shaving device;

wherein the shape-changing smart material is configured, arranged and effective to adapt, by means of a change of its shape and/or dimensions, a relative position and/or a relative orientation between at least part of the skin-contacting surface structure and at least part of the hair-cutting area.

Thanks to the fact that a very limited volume of this special shape-changing smart material of the said class is able already to very quickly respond to said kinds of stimuli, it is possible that this material, for achieving the objects of the invention, is incorporated in the generally very small parts of shaving devices at or around the areas of the skin-contacting and/or hair-cutting areas of the devices. Thanks to the use of this material for adapting the relative position and/or relative orientation between at least part of the skin-contacting surface structure and at least part of the hair-cutting area, the invention makes it possible to instantaneously adapt the abovementioned "closeness" at all times during use of the shaving device, in a skin-location-dependent and time-dependent manner. Hence, the invention provides a powerful tool to dynamically adapt said closeness during a shaving treatment in a manner enabling shaving as close as possible to the skin, with little or no skin irritation. This powerful tool, as provided by the invention, makes it considerably easier for users to obtain a favourable closeness/irritation balance.

As used herein, the said shape-changing smart material of the said class, enabling the material to reversibly change its shape and/or dimensions in a controlled way as a result of an externally applied electrical stimulus and/or as a result of an externally applied thermal stimulus and/or as a result of an externally applied magnetic stimulus and/or as a result of an externally applied chemical stimulus and/or as a result of an externally applied optical stimulus, includes the following sub-classes:
 electro-active polymers,
 electro-active composites,
 electrostrictive ceramics or crystals,
 shape memory metals,
 shape memory polymers,
 photomechanical materials,
 magnetostrictive materials,
 chemo-mechanical materials
 bimetal composites.

The abovementioned sub-class "electro-active polymers" includes, but is not limited to, the sub-sub-classes: piezoelectric polymers, electromechanical polymers, relaxor ferroelectric polymers, electrostrictive polymers, dielectric elastomers, liquid crystal elastomers, conjugated polymers, Ionic Polymer Metal Composites, ionic gels and polymer gels. The sub-sub-class "electrostrictive polymers" includes, but is not limited to: Polyvinylidene fluoride (PVDF), Polyvinylidene fluoride-trifluoroethylene (PVDF-TrFE), Polyvinylidene fluoride-trifluoroethylene-chlorofluoroethylene (PVDF-TrFE-CFE), Polyvinylidene fluoride-trifluoroethylene-chlorotrifluoroethylene) (PVDF-TrFE-CTFE), Polyvinylidene fluoride-hexafluoropropylene (PVDF-HFP) , polyurethanes or blends thereof. The sub-sub-class "dielectric elastomers" includes, but is not limited to: acrylates, polyurethanes, silicones. The sub-sub-class "conjugated polymers" includes, but is not limited to: polypyrrole, poly-3,4-ethylenedioxythiophene, poly(p-phenylene sulfide), polyanilines.

The abovementioned sub-class "electro-active composites" includes, but is not limited to: polymer matrix composites containing piezoelectric, electrostrictive or magnetostrictive particles, carbon nanotubes, nano-fibers or nano-wires and ionic polymer-metal composites.

The abovementioned sub-class "electrostrictive ceramics or crystals" includes, but is not limited to: lead magnesium niobate-lead titanate, lead zinc niobate-lead titanate, barium titanate, lead zirconium titanate, sodium potassium niobate, sodium potassium lithium niobate, sodium bismuth titanate-barium titanate.

The abovementioned sub-class "shape memory metals" includes, but is not limited to: nickel-titanium alloy Nitinol, copper-nickel-titanium.

The abovementioned sub-class "shape memory polymers" includes, but is not limited to: polyurethanes, polyethylene terephthalate (PET) and polyethyleneoxide (PEO) block co-polymers and crosslinked PET and PMMA-based systems.

The abovementioned sub-class "photomechanical materials" includes, but is not limited to: liquid crystal elastomers, azobenzene-containing polymers.

The abovementioned sub-class "magnetostrictive materials" includes, but is not limited to: Terfenol-D and Galfenol alloys.

The abovementioned sub-class chemo-mechanical materials includes, but is not limited to hydrogels and crosslinked hydrogels.

The abovementioned sub-class "bimetal composites" includes, but is not limited to: a dual alloy layered composite in which the first alloy is a high thermal expansion metal, such as brass, steel or stainless steel and the second alloy is a low thermal expansion alloy such as Invar.

Preferably, the shape-changing smart material is configured, arranged and effective to adapt, by means of said change of its shape and/or dimensions:
 said relative position between at least part of the skin-contacting surface structure and at least part of the hair-cutting area by relative displacements of at least 0.001 millimeter, more preferably by relative displacements of at least 0.01 millimeter, yet more preferably by relative displacements of at least 0.05 millimeter, and still further preferably by relative displacements of at least 0.1 millimeter; and/or
 said relative orientation between at least part of the skin-contacting surface structure and at least part of the hair-cutting area by relative rotations through an angle of at least 0.01 degrees, more preferably by relative rotations through an angle of at least 0.1 degrees, yet more preferably by relative rotations through an angle of at least 0.5 degrees, and still further preferably by relative rotations through an angle of at least 1.0 degrees.

In a preferable embodiment of the invention, the shape-changing smart material is part of, or connected to, the skin-contacting structure in such a manner that an adaptation of said relative position and/or relative orientation already occurs without the skin-contacting surface structure contacting any portion of skin. In a further preferable embodiment of the invention, the shape-changing smart material is part of or connected to the cutter in such a manner that an adaptation of said relative position and/or relative orientation already occurs without the skin-contacting surface structure contacting any portion of skin.

In these two preferable embodiment classes, said relative position and/or relative orientation is adapted in an effective and well-defined manner and independently of whether (and how firmly) a user holds the shaving device against the skin.

In a yet further preferable embodiment of the invention, the shaving device further comprises a first resilient suspension structure by which the skin-contacting structure is resiliently suspended relative to at least a housing part of the shaving device, and wherein the shape-changing smart material is part of or connected to said first resilient suspension structure in such a manner as to adapt, by means of said change of its shape and/or dimensions resulting from said at least one stimulus, a spring stiffness of said first resilient suspension structure. In a yet further preferable embodiment of the invention, the shaving device further comprises a second resilient suspension structure by which the cutter is resiliently suspended relative to at least a housing part of the shaving device, and wherein the shape-changing smart material is part of or connected to said second resilient suspension structure in such a manner as to adapt, by means of said change of its shape and/or dimensions resulting from said at least one stimulus, a spring stiffness of said second resilient suspension structure.

In the last-mentioned two preferable embodiment classes, said relative position and/or relative orientation are adapted when a user presses the shaving device against the skin. That is to say, if the spring stiffness of the first and/or the second resilient suspension structure are for example decreased, the resiliently suspended skin-contacting structure and/or the resiliently suspended cutter, respectively, will displace more in response to a certain pressure with which the user presses the shaving device against the skin.

It is noted that said adaptations of the spring stiffness may be obtained in various manners based on the shape-changing smart material. For example, the resilient suspension structure (e.g. a spring) may be made of or coated with the shape-changing smart material, or the shape-changing smart material may be connected in various ways to the resilient suspension structure.

In a further preferable embodiment of the invention, the shape-changing smart material is an electro-active material, i.e. a material which can reversibly change its shape and/or dimensions in a controlled way as a result of an externally applied electrical stimulus.

In a yet further preferable embodiment of the invention, the shape-changing smart material is an electro-active polymer. Electro-active polymers offer extremely quick response times to electric stimuli, while they provide significant usable displacements, and require only an extremely small volume of this special shape-changing smart material.

In a still further preferable embodiment of the invention, the shaving device further comprises a user interface, which is communicatively connected to said controller for controlling said activation of the shape-changing smart material based on user input provided to the user interface. In this way, a user may directly control the activation of the shape-changing smart material by means of (e.g., a button of) the user interface.

In a yet further preferable embodiment of the invention, the shaving device further comprises an electric motor for driving the cutter, wherein the controller is communicatively connected to the electric motor for controlling said activation of the shape-changing smart material based on a motor current during shaving of said skin by the shaving device. Note that in use of the shaving device, a high current of the said electric motor is indicative of long hairs and/or high hair density. Thus, for example, in the case of the relatively high motor currents occurring during the beginning of a shaving session, when the hair is relatively long, the controller may control the device to cut the hairs relatively far from the skin. Then, as during the shaving session the hairs get shorter and shorter, the motor current decreases, based on which the controller may control the device to cut the hairs closer to the skin.

In a yet further preferable embodiment of the invention, the shaving device further comprises a sensor which is communicatively connected to said controller and which is configured, arranged and effective to sense and/or measure, during shaving of said skin by the shaving device, at least one condition of the skin, and wherein the controller is configured, arranged and effective to control said activation of the shape-changing smart material based on said at least one skin condition sensed and/or measured by said sensor. Said at least one skin condition sensed and/or measured by said sensor may for example be skin colour (e.g. redness of the skin caused by skin irritation) and/or hair density and/or hair length and/or skin pressure and/or skin doming and/or frictional resistance relative to said skin-contacting surface structure.

In a yet further preferable embodiment of the invention, the shaving device is a rotary shaver. Preferably, the rotary shaver comprises at least one cutting unit, which cutting unit comprises an external cutting member and an internal cutting member which is rotatable around a rotation axis relative to the external cutting member, said hair-cutting area thus being an annular moving trajectory of cutting edges of the internal cutting member, said moving trajectory extending along the external cutting member and around said rotation axis, and wherein, as seen in perpendicular projection onto a hypothetical plane, being perpendicular to said rotation axis, at least part of the shape-changing smart material is surrounded by said hair-cutting area for reversibly displacing, relative to said hair-cutting area, and at least with a component in a direction parallel to said rotation axis, at least a portion of the skin-contacting surface structure, which portion is also surrounded by said hair-cutting area. The special location of said displacing portion of the skin-contacting surface being surrounded in the said sense by said annular hair-cutting area is a very effective location providing a very large effective surface-area of said portion for contacting skin. Its location also is very effective relative to the annular hair-cutting area.

In a yet further preferable embodiment of the invention, the shaving device is a razor blade system which comprises a guard and a handle and wherein the cutter comprises at least one cutting blade mounted within the guard. The abovementioned advantages of a shaving device according to the invention work out very well in such a razor blade system, especially because of the compact and often detachable nature of the guard.

In a yet further preferable embodiment of the invention, the shaving device is a laser beam shaver, wherein the cutter is a laser beam cutter which is configured, arranged and effective to focus a hair-cutting laser beam in the hair-cutting area. The abovementioned advantages of a shaving device according to the invention work out very well in such a laser beam shaver, especially because the quick response times of the shape-changing smart material match very well with the automatic character of laser beam shavers and with the non-mechanical character of their laser beam cutters.

BRIEF DESCRIPTION OF THE DRAWINGS

The abovementioned aspects and other aspects of the invention will be apparent from and elucidated with reference to the embodiments described hereinafter by way of non-limiting examples only and with reference to the highly schematic figures in the enclosed drawing.

It is noted that the same reference signs are used in FIGS. 1-8B to denote the same or similar parts or aspects.

DETAILED DESCRIPTION OF EMBODIMENTS

Figure 6A:
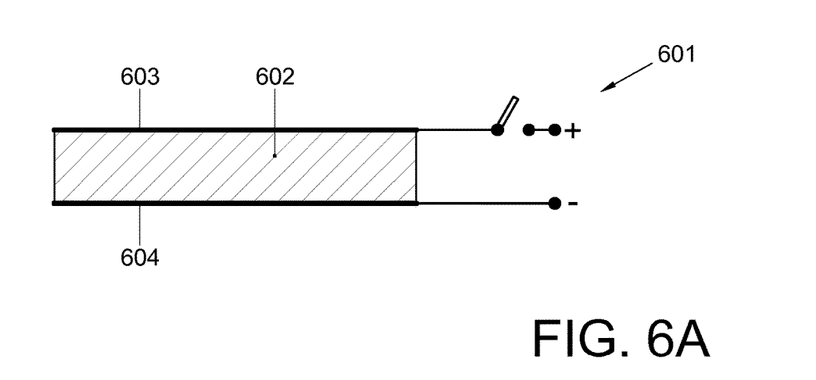
FIG. 6A shows an example of an embodiment of a compression actuator for use in a shaving device according to the invention, wherein the compression actuator comprises a shape-changing smart material in the form of an electro-active polymer, and wherein the compression actuator is in its undeformed condition.

As an introduction to the detailed description of embodiments of the shaving device according to the invention, reference is first made to FIGS. 6A/6B, 7A/7B, and 8A/8B, which illustrate, as non-limiting examples, three different types of actuators for use in shaving devices according to the invention. All three actuators comprise electro-active polymers as the shape-changing smart material for use in the invention. The three examples show layers of the electro-active polymer and layers of conductive electrodes on top and to the bottom of each electro-active polymer layer, while FIGS. 8A/8B additionally show a substrate layer. All FIGS. 6A/6B, 7A/7B, and 8A/8B are side views of these layers.

Figure 6B:
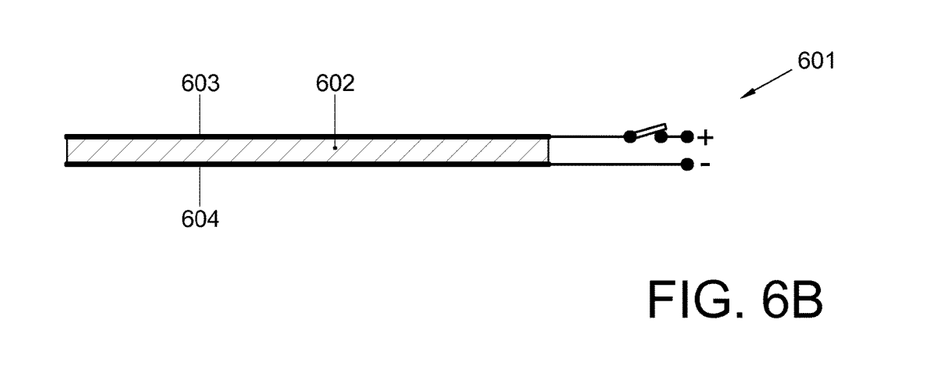
FIG. 6B shows the situation of FIG. 6A once again, however, this time in a deformed condition of the compression actuator.

The compression actuator 601 of FIGS. 6A/6B comprises an electro-active polymer layer 602 which is sandwiched between the conductive electrodes 603 and 604. As can be seen, when an electric field is applied to the active polymer layer 602, it changes shape by contracting in the direction of the applied electric field and expanding perpendicularly to the electric field. The usable force and displacement from this compression actuator 601 are directed in the direction of the electric field.

Figure 7A:
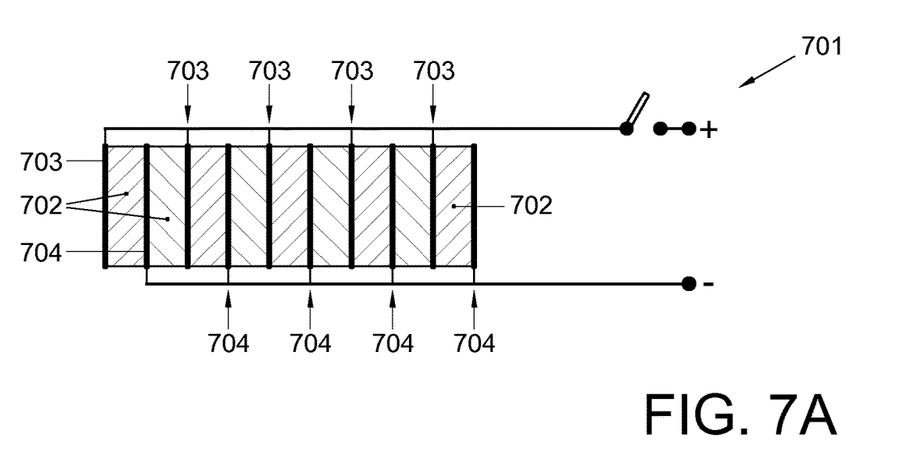
FIG. 7A shows an example of an embodiment of a lateral extension actuator for use in a shaving device according to the invention, wherein the lateral extension actuator comprises a shape-changing smart material in the form of an electro-active polymer, and wherein the lateral extension actuator is in its undeformed condition.
Figure 7B:
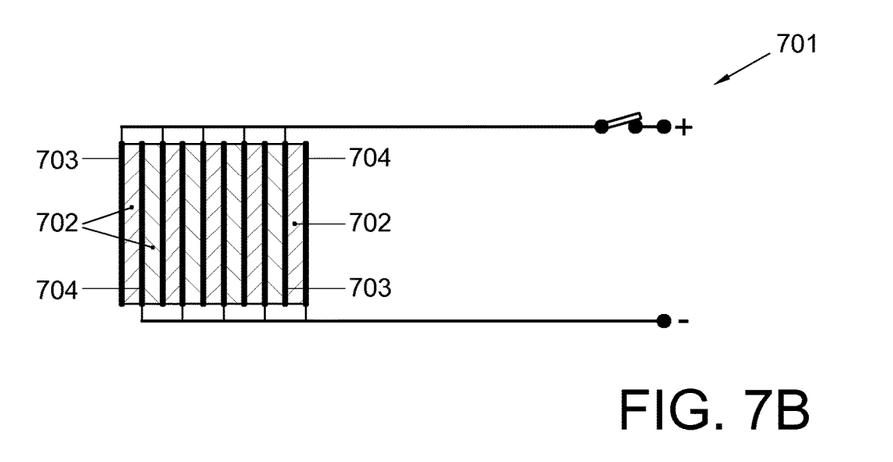
FIG. 7B shows the situation of FIG. 7A once again, however, this time in a deformed condition of the lateral extension actuator.

The lateral extension actuator 701 of FIGS. 7A/7B comprises a stack of electro-active polymer layers 702, each of which is contacted by conductive electrodes 703 and 704 on opposite sides thereof. When an electric field is applied to each layer 702, it changes shape by contracting in the direction of the applied electric field and expanding perpendicularly to the electric field. The usable force and displacement from this lateral extension actuator 701 are directed perpendicularly to the direction of the electric field.

Figure 8A:
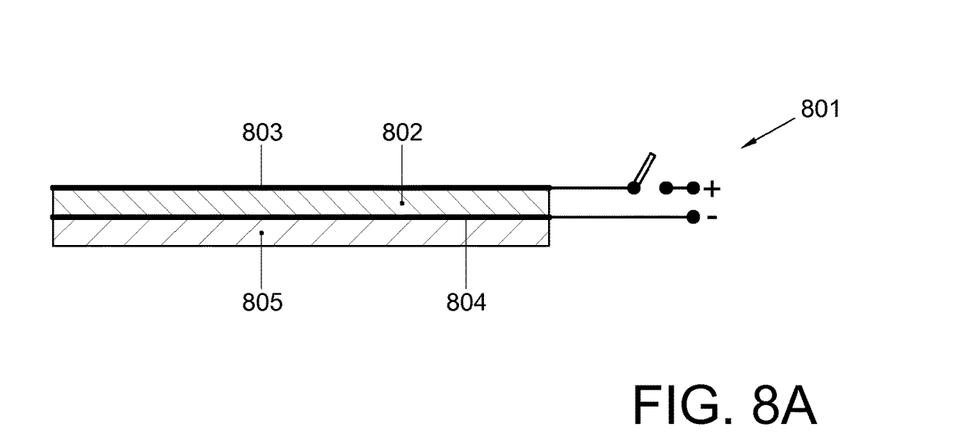
FIG. 8A shows an example of an embodiment of a bending actuator for use in a shaving device according to the invention, wherein the bending actuator comprises a shape-changing smart material in the form of an electro-active polymer, and wherein the bending actuator is in its undeformed condition.
Figure 8B:
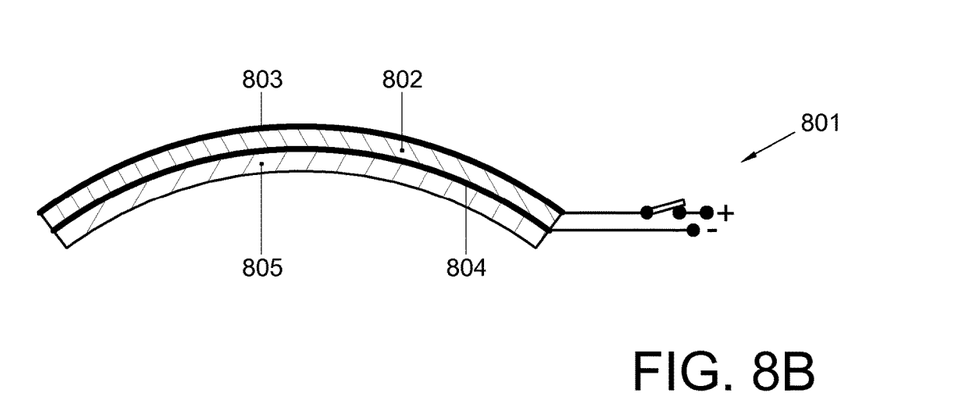
FIG. 8B shows the situation of FIG. 8A once again, however, this time in a deformed condition of the bending actuator.

In the bending actuator 801 of FIGS. 8A/8B, the electro-active polymer layer 802 is sandwiched between the conductive electrodes 803 and 804, and this sandwiched package is connected to the substrate 805. When an electric field is applied to the electro-active polymer layer 802, it contracts in the direction of the electric field, while it expands laterally. The substrate 805, however, constrains the lateral expansion, thereby causing a bending motion of the actuator. The usable force and displacement from this bending actuator 801 are in the direction of the electric field. It is noted that such a bending actuator, instead of having only one electro-active polymer layer, may also have a stack of layers of electro-active polymer material, wherein the stack is connected to the substrate.

Figure 1:
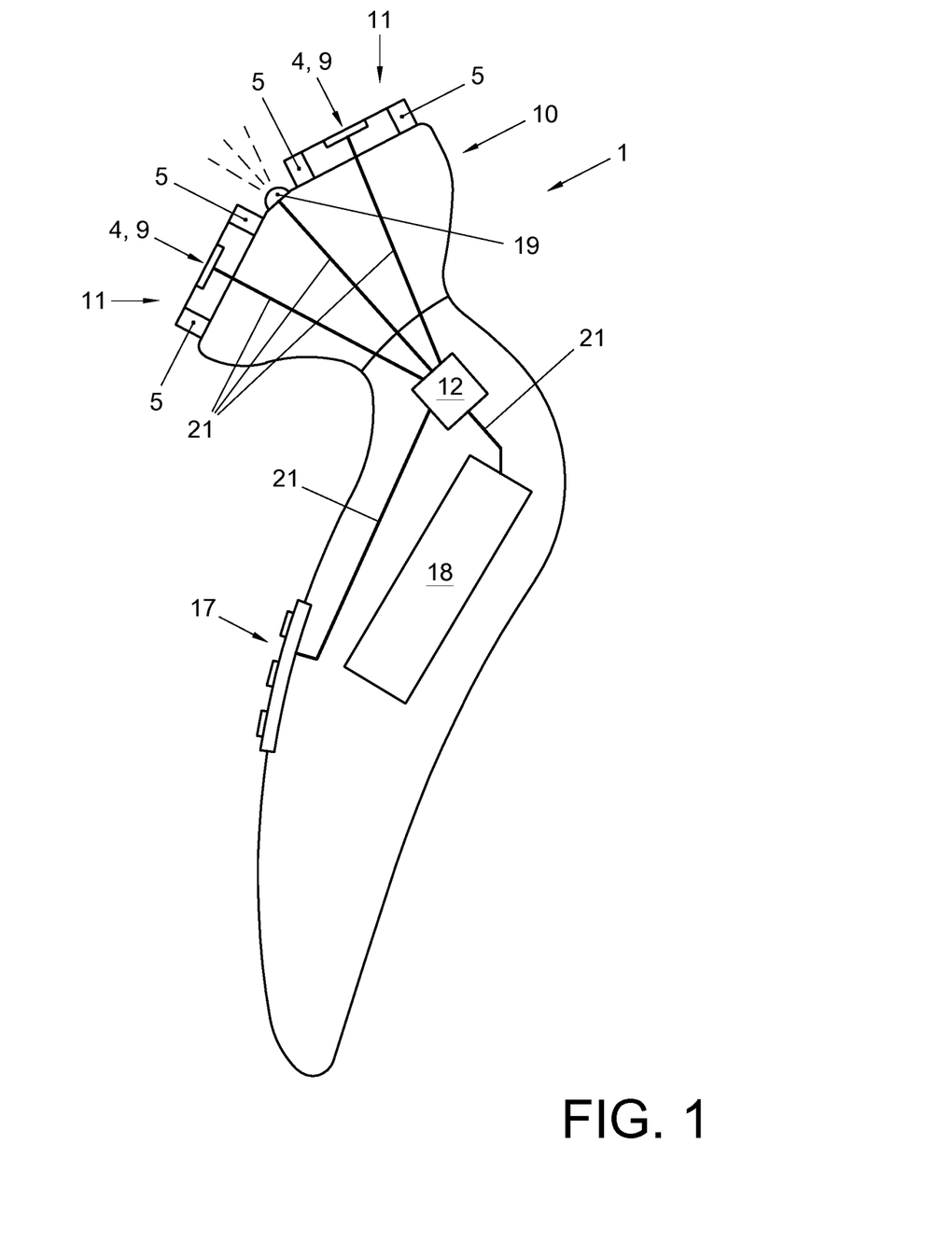
FIG. 1 shows, in a cross-sectional view, an example of an embodiment of a shaving device according to the invention, the shown device being of the "rotary shaver" type.
Figure 2:
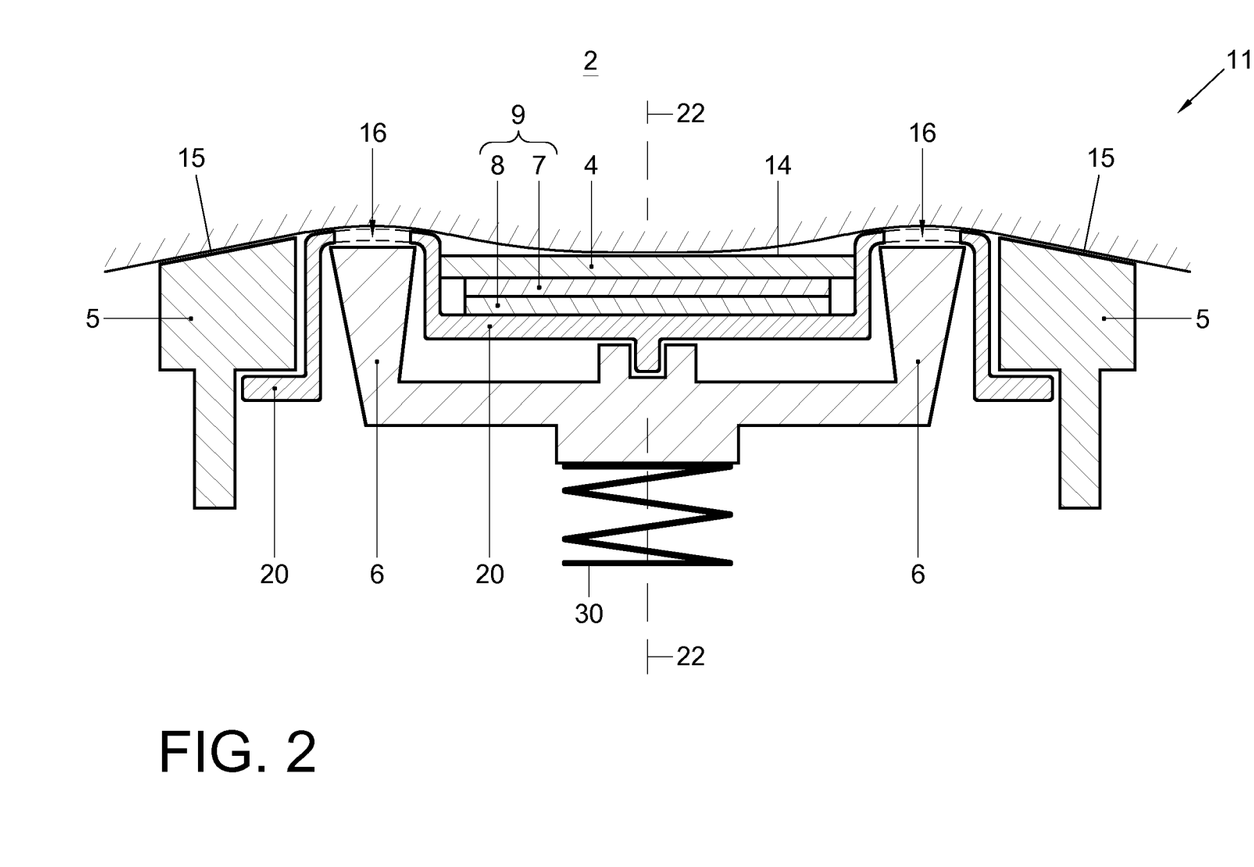
FIG. 2 shows, in a cross-sectional view, one of the cutting units of the shaving head of the shaving device of FIG. 1 in undeformed condition of a bending actuator which is incorporated in the cutting unit and which comprises a shape-changing smart material in the form of an electro-active polymer. The cutting unit is shown while being held against a person's skin.
Figure 3:
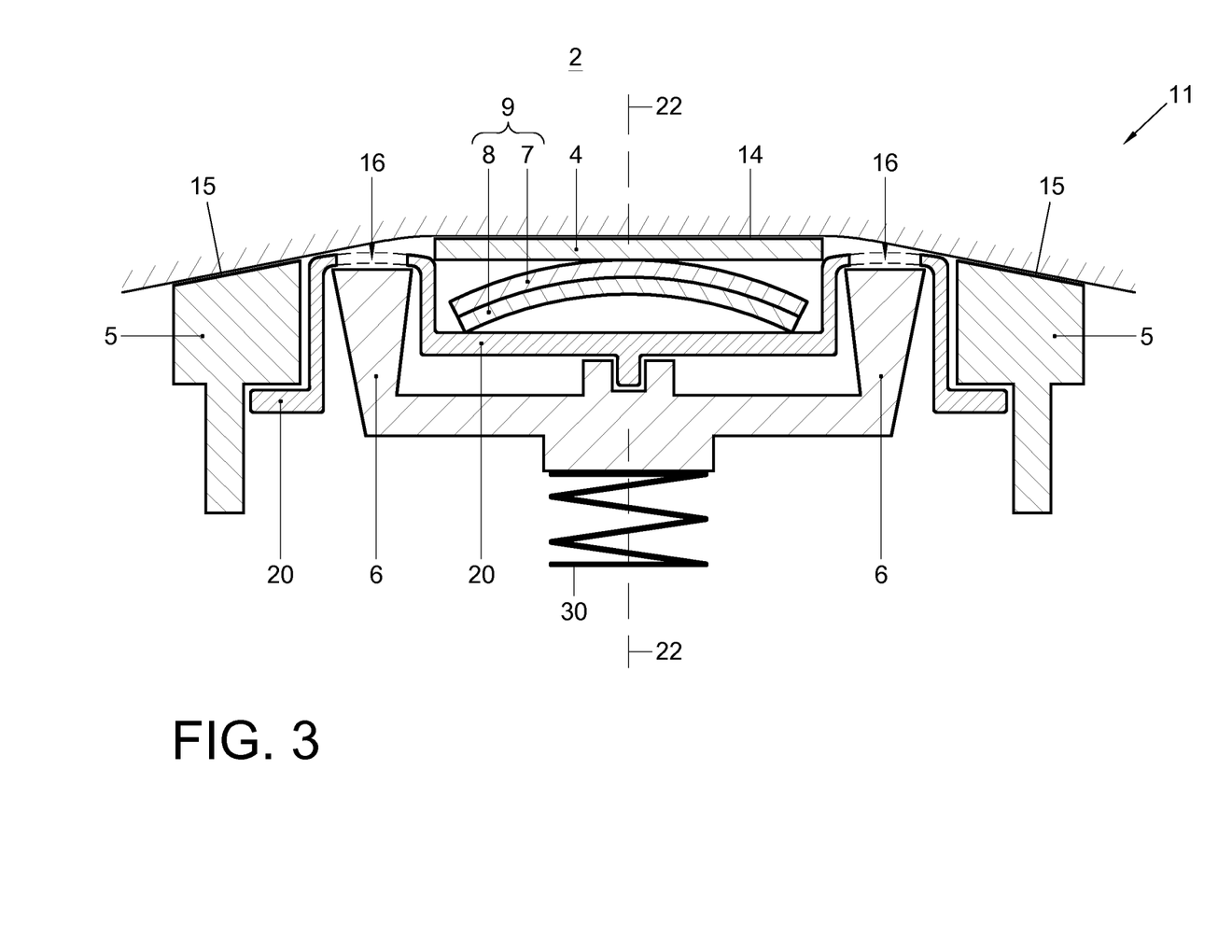
FIG. 3 shows the situation of FIG. 2 once again, however, this time in a deformed condition of the bending actuator.

Now, reference is made to FIGS. 1, 2, 3, which illustrate an example of an embodiment of a shaving device according to the invention, in this case the rotary shaver 1.

The shaver 1 has a shaving head 10, which has a number of identical cutting units 11, two of which are shown in FIG. 1, and one of which is shown in more detail in FIGS. 2 and 3. The cutting unit 11 has a well-known main structure comprising a skin supporting ring 5, which surrounds an assembly of an external cutting member 20 and an internal cutting member 6. The internal cutting member 6 is pressed with its cutting edges against the external cutting member 20. This pressing usually is realized by means of a spring mounted within the shaving head 10. In a very schematical manner, such a spring is indicated in FIGS. 2, 3 by means of the shown helical spring 30. The pressing contact between the internal cutting member 6 and the external cutting member 20 occurs at an annular area of the external cutting member 20, which annular area has hair openings therethrough. In use, a drive shaft (not shown) causes rotation of the internal cutting member 6, around the shown rotation axis 22, in such a manner that the cutting edges of the internal cutting member 6 move along the hair openings of the external cutting member 20. Accordingly, an annular hair-cutting area 16 is defined by the annular working area of the cutting edges of the internal cutting member 6.

In the shown example, the skin supporting ring 5 is part of the abovementioned skin-contacting structure, as recited above for a shaving device according to the invention. The skin supporting ring 5 has a first skin-contacting surface, indicated by the reference numeral 15, which is part of the skin-contacting surface structure of the skin-contacting structure. In FIGS. 2 and 3, it can be seen that the skin 2 of a person lies at least partly against this first skin-contacting surface 15 of the skin supporting ring 5.

The skin-contacting structure of the shaver 1 further comprises, for each cutting unit 11, a skin supporting disc, indicated by the reference numeral 4 in FIGS. 2 and 3. This skin supporting disc 4 has a second skin-contacting surface, indicated by the reference numeral 14, which is part of the skin-contacting surface structure of the skin-contacting structure. In FIGS. 2 and 3, it can be seen that the skin 2 of a person also lies at least partly against this second skin-contacting surface 14 of the skin supporting disc 4.

Each cutting unit 11 further comprises a bending actuator 9 of the type 801 as shown and discussed above in relation to FIGS. 8A/8B. That is to say, the disc-shaped layer 7 of FIG. 2 corresponds to the electro-active polymer layer 802 of FIG. 8A, while the disc-shaped layer 8 of FIG. 2 corresponds to the substrate 805 of FIG. 8A. For simplicity, the conductive electrodes, corresponding to the conductive electrodes 803 and 804, are not shown in FIGS. 2/3. The bending actuator 9 is located in a disc-shaped recessed central portion of the external cutting member 20 between the external cutting member 20 and the skin supporting disc 4. From FIGS. 2/3 it is clear that the usable force and displacement from this bending actuator 9 are directed parallel to the rotation axis 22. Furthermore, FIGS. 2/3 make clear that the bending actuator 9, based on the shape-changing smart material 7, is able to adapt the relative position and/or relative orientation between the second skin-contacting surface 14 and the annular hair-cutting area 16. Note that in FIG. 3 the skin 2 is held farther away from the hair-cutting area 16 than in FIG. 2. Accordingly, the condition of FIG. 3 leads to reduced skin irritation as compared to the condition of FIG. 2.

In FIG. 1, reference numeral 12 indicates the abovementioned controller for controlling activation of the shape-changing smart material (here the electro-active polymer layers 7 of the bending actuators 9 of the cutting units 11) during use of the shaving device 1. Furthermore, in FIG. 1, the reference numerals 17, 18, and 19 indicate the above-mentioned user interface, electric motor, and sensor, respectively. The lines 21, shown in FIG. 1, schematically indicate communicative connections between the controller 12, on the one hand, and the bending actuators 9, the user interface 17, the motor 18, and the sensor 19, respectively, on the other hand.

In the shown example, the electro-active polymer layer 7 may be for example of PVDF or PVDF-TrFE-CTFE, while the disc-shaped substrate layer 8 may be for example a polymer such as PET, PEN, PI or PEEK or a metal film such as (stainless) steel, copper, aluminium. Based on these kinds of materials, tests have been performed with prototypes of the bending actuator 9, in which the actuator thickness was about 1 mm and the diameter was about 13 mm. This resulted in usable displacements of about 0.2 mm, and a usable force of about 1 N per actuator.

It is remarked that in the example of FIGS. 1, 2, 3, the helical spring 30, in addition to its function of pressing the internal cutting member 6 with its cutting edges against the external cutting member 20, also functions as the above-mentioned first resilient suspension structure by which the skin-contacting structure is resiliently suspended relative to at least a housing part of the shaving device. Hence, it is possible that shape-changing smart material of the class recited in the present invention is part of or connected to the helical spring 30, for example in that the spring 30 has a coating of the shape-changing smart material. This would allow the stiffness of the spring 30 to be made adaptable via applying stimuli to the shape-changing smart material.

Figure 4:
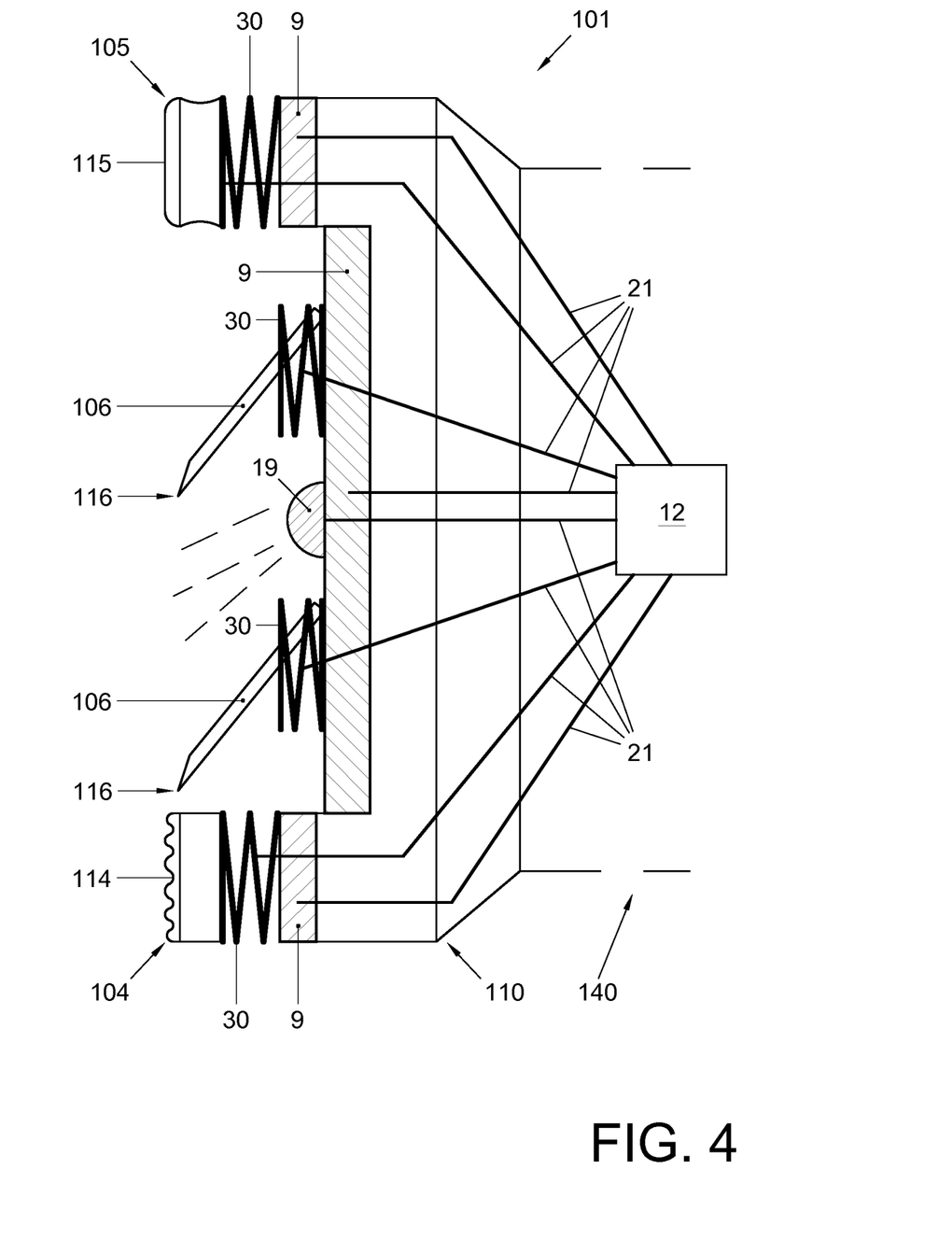
FIG. 4 shows, in a cross-sectional view, an example of another embodiment of a shaving device according to the invention, the shown device being of the "razor blade system" type (for wet shaving).

Next, reference is made to FIG. 4, which illustrates an example of another embodiment of a shaving device according to the invention, in this case the razor blade system 101, which is suitable for wet shaving.

The razor blade system 101 has a well-known main structure, which comprises a guard 110 and a handle 140 (for simplicity, only a small part of the handle 140 is shown near its connection with the guard 110). A pair of cutting blades 106 is mounted within the guard 110. The cutting edges of these cutting blades 106 define the hair-cutting areas 116. Furthermore, the guard comprises a skin stretcher 104 and a lubricity element 105. The skin stretcher 104 and the lubricity element 105 are part of the abovementioned skin-contacting structure, as recited above for a shaving device according to the invention, while their skin-contacting surfaces 114 and 115, respectively, are part of the skin-contacting surface structure of that skin-contacting structure.

FIG. 4 illustrates various ways in which the shape-changing smart material of the class as recited for a shaving device according to the present invention may be applied in the shaving device, in this case in the razor blade system 101.

In FIG. 4, reference numeral 30 indicates a resilient suspension structure by which an element of the skin-contacting structure or of the cutter of the system 101 is, or may be, resiliently suspended relative to at least a housing part of the system 101. In the example, this resilient suspension is shown for the skin stretcher 104, for the lubricity element 105, and for each one of the cutting blades 106. More in particular, and by way of non-limiting example only, in FIG. 4 this resilient suspension structure is illustrated by means of a helical spring 30 similar to the helical spring 30 shown in the example of FIGS. 1, 2, 3. Again similar to the example of FIGS. 1, 2, 3, for each of these helical springs 30 of FIG. 4, it is possible that shape-changing smart material of the class recited in the present invention is part of or connected to the helical spring 30, for example in that the spring 30 has a coating of the shape-changing smart material. As a result, the stiffness of the spring 30 could be made adaptable via applying stimuli to the shape-changing smart material.

In FIG. 4, reference numeral 9 indicates an actuator, which is based on the shape-changing smart material of the class recited in the present invention, and which is similar to the actuators 9 shown in FIGS. 1, 2, 3. Note that each actuator 9 of FIG. 4 (as well as of FIGS. 1, 2, 3, 5) may of course be of many different types, such as e.g. the compression actuator type explained with reference to FIGS. 6A/B, the lateral extension actuator type explained with reference to FIGS. 7A/B, the bending actuator type explained with reference to FIGS. 8A/B, or of any other type based on the shape-changing smart material.

FIG. 4 furthermore shows a sensor 19, a controller 12, and communicative connections 21, having functions similar to the sensor 19, controller 12, and communicative connections 21 shown in FIG. 1.

Altogether, it can be seen that the example of FIG. 4 shows various ways of adapting, by means of the said change of the shape and/or dimensions of the shape-changing smart material, the relative position and/or relative orientation between at least part of the skin-contacting surface structure and at least part of the hair-cutting area. In fact, FIG. 4 shows examples of how the shape-changing smart material may be part of or connected to the skin-contacting structure (cf. the actuator 9 for the skin stretcher 104 and the actuator 9 for the lubricity element 105) and/or the cutter (cf. the actuator 9 for the cutting blades 106) in such a manner that said adaptation of said relative position and/or relative orientation already occurs without the skin-contacting surface structure contacting any portion of skin; and/or examples of how the shape-changing smart material may be part of or connected to a first resilient suspension structure by which the skin-contacting structure (cf. the spring 30 for the skin stretcher 104 and the spring 30 for the lubricity element 105) is resiliently suspended relative to at least a housing part of the shaving device and/or a second resilient suspension structure by which the cutter (cf. the springs 30 for the cutting blades 106) is resiliently suspended relative to at least a housing part of the shaving device, in such manner as to adapt, by means of said change of its shape and/or dimensions resulting from said at least one stimulus, the spring stiffness of said resilient suspension structure.

Figure 5:
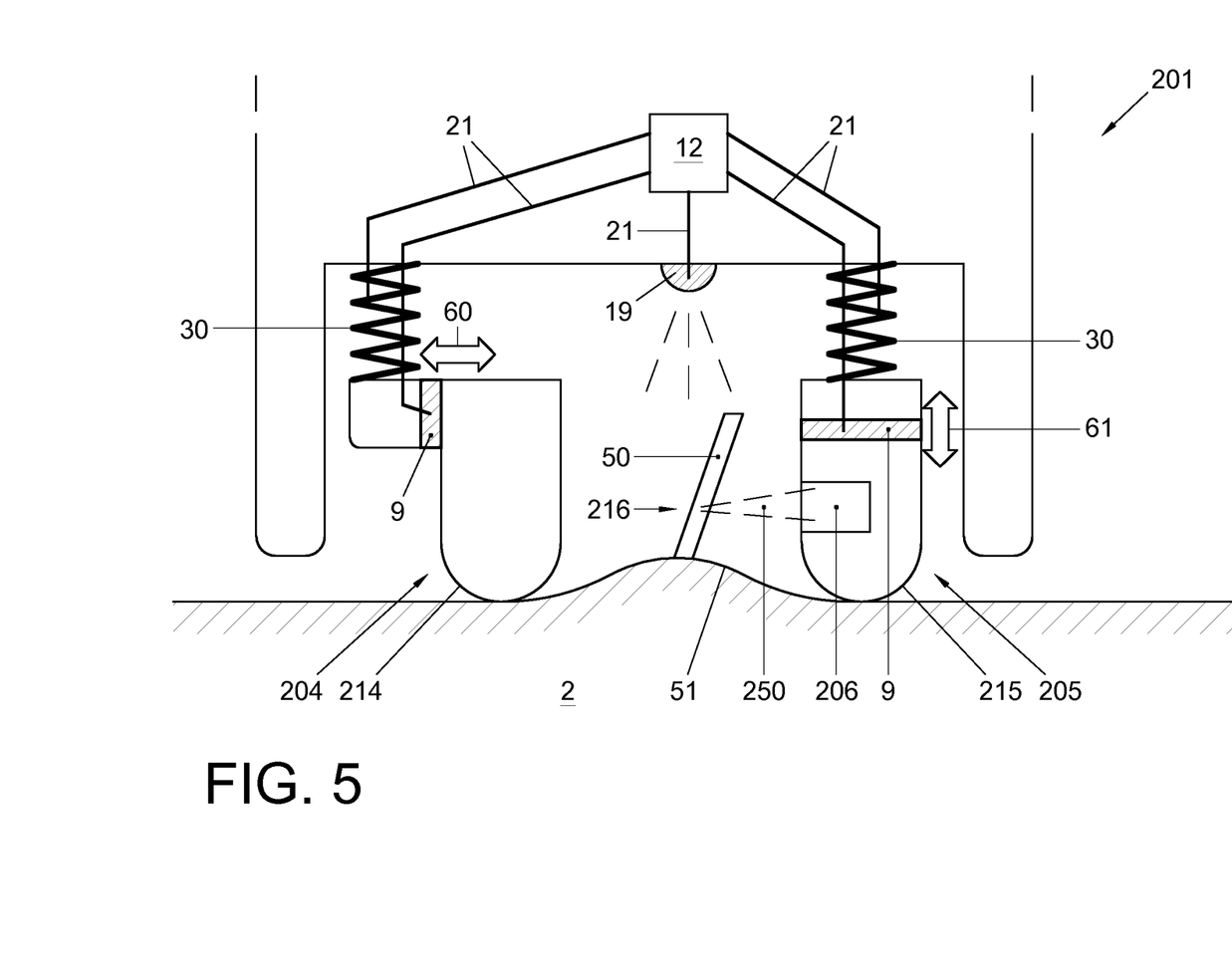
FIG. 5 shows, in a cross-sectional view, an example of yet another embodiment of a shaving device according to the invention, the shown device being of the "laser beam shaver" type.

Next, reference is made to FIG. 5, which illustrates an example of yet another embodiment of a shaving device according to the invention, in this case the laser beam shaver 201. In FIG. 5, the reference numeral 9 indicates an actuator, which is based on the shape-changing smart material of the class recited in the present invention, and which is similar to the actuators 9 shown in FIGS. 1, 2, 3, 4.

The cutter of the shaver 201 is indicated by reference numeral 206. This laser beam cutter 206 comprises optical elements like mirrors, reflectors and lenses for directing a hair-cutting laser beam 250 through an exit window of the cutter 206 and focusing this laser beam 250 in the hair-cutting area 216. FIG. 5 shows a hair 50 extending from a skin dome 51 of the skin 2, which skin dome has been formed in the slit between the two shown skin-contacting elements 204 and 205 of the skin-contacting structure of the shaver 201. These skin-contacting elements 204 and 205 have skin-contacting surfaces 214 and 215, respectively, which are part of the skin-contacting surface structure of the shaver 201. The shaver 201 of FIG. 5 comprises a controller 12, a sensor 19, communicative connections 21, actuators 9, helical springs 30, all in a similar manner and having similar functions as explained for the system 101 of FIG. 4. The two-direction arrows 60 and 61 indicate the reciprocating displacement directions from the actuators 9 applied in the skin-contacting elements 204 and 205, respectively. As a non-limiting example, in FIG. 5 the actuators 9 have been configured and arranged such that the reciprocating displacement directions 60 and 61 are mutually orthogonal. Thus, it is possible to control relative height differences between the two skin-contacting surfaces 214 and 215, as well as to control the width of the slit between the skin-contacting elements 204 and 205, thereby influencing, e.g., the shape of the skin dome 51.

While the invention has been described and illustrated in detail in the foregoing description and in the drawing figures, such description and illustration are to be considered exemplary and/or illustrative and not restrictive; the invention is not limited to the disclosed embodiments.

For example, the shape-changing smart material may also be used for providing sensor functionalities of the sensors as discussed herein. Furthermore, it is possible to apply, instead of or in addition to the discussed helical springs, various other types of springs or resilient structures. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. For the purpose of clarity and a concise description, features are disclosed herein as part of the same or separate embodiments, however, it will be appreciated that the scope of the invention may include embodiments having combinations of all or some of the features disclosed. The mere fact that certain measures are recited in mutually different dependent claims does not indicate that a combination of these measures can not be used to advantage. Any reference signs in the claims should not be construed as limiting the scope.

The invention claimed is:

1. A shaving device for skin hairs, comprising:
    a skin-contacting structure comprising a skin-contacting surface structure for contacting a portion of skin during shaving of said skin by the shaving device;
    a cutter for cutting hairs of said skin portion being contacted by said skin-contacting surface structure, said cutting taking place in a hair-cutting area defined by the shaving device;
    a shape-changing smart material of a class of materials that can reversibly change their shape and/or dimensions in a controlled way as a result of an externally applied electric stimulus and/or as a result of an externally applied thermal stimulus and/or as a result of an externally applied magnetic stimulus and/or as a result of an externally applied chemical stimulus and/or as a result of an externally applied optical stimulus; and
    a controller for controlling activation of the shape-changing smart material during use of the shaving device;
    wherein the shape-changing smart material is configured, arranged and effective to adapt, by means of a change of its shape and/or dimensions, a relative position and/or a relative orientation between at least part of the skin-contacting surface structure and at least part of the hair-cutting area.

2. A shaving device according to claim 1, wherein the shape-changing smart material is part of or connected to the skin-contacting structure in such a manner that an adaptation of said relative position and/or relative orientation already occurs without the skin-contacting surface structure contacting any portion of the skin.

3. A shaving device according to claim 1, wherein the shape-changing smart material is part of or connected to the cutter in such a manner that an adaptation of said relative position and/or relative orientation already occurs without the skin-contacting surface structure contacting any portion of the skin.

4. A shaving device according to claim 1, further comprising a first resilient suspension structure by which the skin-contacting structure is resiliently suspended relative to at least a housing part of the shaving device, and wherein the shape-changing smart material is part of or connected to said first resilient suspension structure in such a manner as to adapt, by means of said change of its shape and/or dimensions resulting from said at least one stimulus, a spring stiffness of said first resilient suspension structure.

5. A shaving device according to claim 1, further comprising a resilient suspension structure by which the cutter is resiliently suspended relative to at least a housing part of the shaving device, and wherein the shape-changing smart material is part of or connected to said resilient suspension structure in such a manner as to adapt, by means of said change of its shape and/or dimensions resulting from said at least one stimulus, a spring stiffness of said resilient suspension structure.

6. A shaving device according to claim 1, wherein the shape-changing smart material is an electro-active material, which can reversibly change its shape and/or dimensions in a controlled way as a result of the externally applied electric stimulus.

7. A shaving device according to claim 6, wherein the shape-changing smart material is an electro-active polymer.

8. A shaving device according to claim 1, further comprising a user interface which is communicatively connected to said controller for controlling said activation of the shape-changing smart material based on user input provided to the user interface.

9. A shaving device according to claim 1, further comprising an electric motor for driving the cutter, and wherein the controller is communicatively connected to the electric motor for controlling said activation of the shape-changing smart material based on a motor current during shaving of said skin by the shaving device.

10. A shaving device according to claim 1, further comprising a sensor which is communicatively connected to said controller and which is configured, arranged and effective to sense and/or measure, during shaving of said skin by the shaving device, at least one skin condition of the skin, and wherein the controller is configured, arranged and effective to control said activation of the shape-changing smart material based on said at least one skin condition sensed and/or measured by said sensor.

11. A shaving device according to claim 10, wherein said at least one skin condition sensed and/or measured by said sensor includes skin colour and/or hair density and/or hair length and/or skin pressure and/or skin doming and/or frictional resistance relative to said skin-contacting surface structure.

12. A shaving device according to claim 1, wherein the shaving device is a rotary shaver.

13. A shaving device according to claim 12, wherein the rotary shaver comprises at least one cutting unit, which cutting unit comprises an external cutting member and an internal cutting member which is rotatable around a rotation axis relative to the external cutting member, said hair-cutting area thus being an annular moving trajectory of cutting edges of the internal cutting member, said moving trajectory extending along the external cutting member and around said rotation axis, and wherein, as seen in perpendicular projection onto a hypothetical plane being perpendicular to said rotation axis, at least part of the shape-changing smart material is surrounded by said hair-cutting area for reversibly displacing, relative to said hair-cutting area, and at least with a component in a direction parallel to said rotation axis, at least a portion of the skin-contacting surface structure, which portion is also surrounded by said hair-cutting area.

14. A shaving device according to claim 1, wherein the shaving device is a razor blade system which comprises a guard and a handle, and wherein the cutter comprises at least one cutting blade mounted within the guard.

15. A shaving device according to claim 1, wherein the shaving device is a laser beam shaver, and wherein the cutter is a laser beam cutter which is configured, arranged and effective to focus a hair-cutting laser beam in the hair-cutting area.

* * * * *